(12) United States Patent
Chen

(10) Patent No.: US 8,599,323 B2
(45) Date of Patent: Dec. 3, 2013

(54) BATTERY LOW-VOLTAGE WARNING APPARATUS FOR AUTO-DARKENING FILTER FOR WELDING HELMET

(76) Inventor: Gang Chen, Vancouver (CA)

( * ) Notice: Subject to any disclaimer, the term of this patent is extended or adjusted under 35 U.S.C. 154(b) by 347 days.

(21) Appl. No.: 12/498,113

(22) Filed: Jul. 6, 2009

(65) Prior Publication Data

US 2013/0174312 A1 Jul. 11, 2013

Related U.S. Application Data

(60) Provisional application No. 61/079,118, filed on Jul. 8, 2008.

(51) Int. Cl.
*G02F 1/1335* (2006.01)
(52) U.S. Cl.
USPC .......................................................... 349/16
(58) Field of Classification Search
USPC .......................................................... 349/16
See application file for complete search history.

(56) References Cited

U.S. PATENT DOCUMENTS

| 6,067,129 | A | 5/2000 | Fergason |
| 2004/0036821 | A1 | 2/2004 | Paukshto |
| 2005/0007667 | A1 | 1/2005 | Fergason |
| 2005/0097648 | A1 | 5/2005 | Ackermann |
| 2007/0081250 | A1 | 4/2007 | Garbergs |
| 2007/0289049 | A1 | 12/2007 | Gerfin |

OTHER PUBLICATIONS

International Preliminary Report on Patentability (Jan. 4, 2012) PCT/CA2009/000922 (Inventor: Gang Chen) Battery Low-Voltage Warning Apparatus for Auto-Darkening Filter . . . .

*Primary Examiner* — Phu Vu
(74) *Attorney, Agent, or Firm* — Clark Wilson LLP; Michael J. Roman

(57) ABSTRACT

An apparatus for annunciating low-voltage in a battery supplying electricity to an auto-darkening optical filter system (10) for a welding helmet (not shown). Low voltage is annunciated by changing, for example strobing, the opacity of the optical filter system (10).

9 Claims, 3 Drawing Sheets

BATTERY LOW-VOLTAGE WARNING APPARATUS FOR AUTO-DARKENING FILTER FOR WELDING HELMET

BACKGROUND OF THE INVENTION

1. Field of the Invention

An apparatus for annunciating low-voltage in a battery supplying electricity to an auto-darkening optical filter system for a welding helmet.

2. Description of the Related Art

A conventional auto-darkening optical filter system for a welding helmet has both an optical band-pass filter that continuously blocks damaging ultraviolet and infrared radiation from reaching a welder's eyes and an auto-darkening LCD shutter that allows essentially all ambient visible light to pass but darkens in the presence of intense visible light—for example during a welding operation—to allow only a portion of the visible light to reach the welder's eyes. In this way, the welder's eyes receive an appropriate amount of visible light to see both during welding operations and otherwise. The band-pass filter and the LCD shutter are stacked one atop the other in series and both are protected by a cover glass.

Considering the LCD shutter in more detail now, an optical sensor detects light intensity proximate the cover glass. An LCD driver electrically connected to both the optical sensor and the LCD shutter applies a variable shuttering voltage to the LCD shutter to cause the LCD shutter to increase its opacity in response to increasing light intensity detected by the optical sensor. This increase in opacity may be a simple change between a transparent state and a translucent state or may be a more gradual change through multiple states of increasing translucency, for more expensive systems.

The electricity that powers such systems is generally provided by battery. It is therefore a common concern that the battery will unexpectedly deplete and be insufficient to power the system. The consequence of this situation would be that the LCD shutter could fail to darken when a welding operation commences and too much visible light could pass through the optical filter system to the welder's eyes, leading to temporary dazing or even eye irritation.

A typical solution to this problem has been to include an indicator light—often an LED—in the system, which illuminates or flashes when the battery voltage falls below a predetermined threshold and is therefore close to being insufficient to power the system. While an improvement, this arrangement has a number of disadvantages. For example, a small light can be difficult to notice in a bright welding environment. Furthermore, illuminating a light—even an energy-efficient LED—depletes the battery further.

What is needed is a way to more certainly announce battery low-voltage to a welder, which does not significantly deplete the battery further.

SUMMARY OF THE INVENTION AND ADVANTAGES

The present invention is directed to such a solution.

According to one aspect of the present invention, there is provided such an auto-darkening optical filter system for a welding helmet having: a low-voltage detection module operable to generate a warning signal in response to detecting low-voltage at the battery and a low-voltage annunciation module operable to announce a battery low-voltage condition in response to the warning signal by applying an annunciating voltage to the LCD shutter to cause the LCD shutter to change its opacity.

The low-voltage detection module might include a voltage reference and a comparator connected between the voltage reference and the battery. The voltage reference might include a photovoltaic cell and a voltage regulator.

The low-voltage annunciation module might include an oscillator to strobe the LCD shutter to cause the LCD shutter to periodically increase and decrease its opacity. The oscillator may include a timer circuit.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Figure 1:
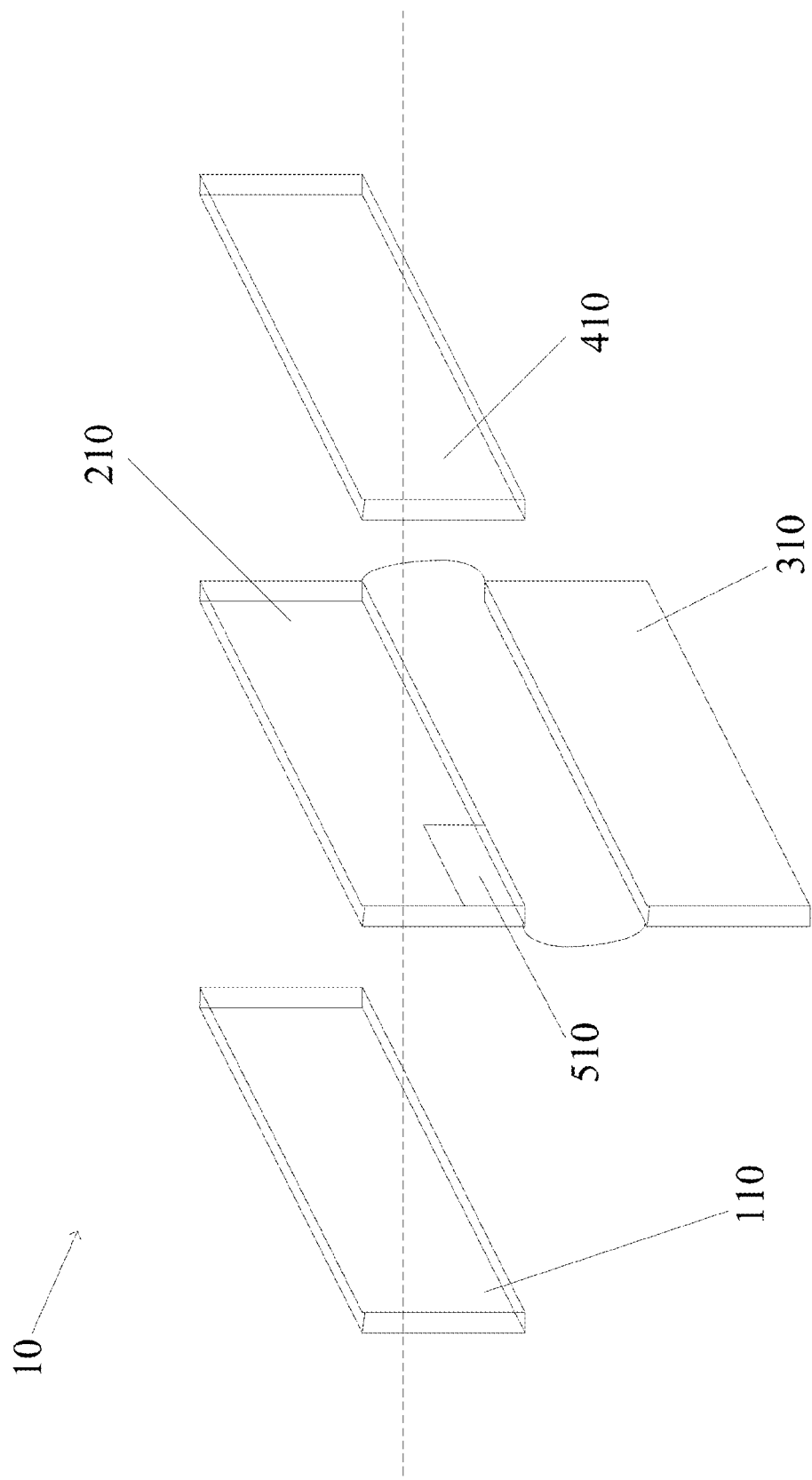
FIG. 1 is an exploded isometric view of one embodiment of an auto-darkening optical filter system according to one aspect of the present invention, the system including an LCD driver.

Referring to the Figures, wherein like numerals indicate corresponding parts throughout the several views, an apparatus for annunciating low-voltage in a battery supplying electricity to an auto-darkening optical filter system 10 for a welding helmet (Not Shown) will now be described.

Structure.

The auto-darkening optical filter system 10 includes an optical band-pass filter 110 to continuously prevent damaging ultraviolet and infrared radiation emitted by a welding operation from reaching a welder's eyes and an auto-darkening LCD shutter 210 that additionally reduces the portion of visible light emitted by the welding operation from reaching the welder's eyes. The band-pass filter 110 and the LCD shutter 210 are stacked one atop the other in series and both are protected by a cover glass 410.

The system 10 also includes an optical sensor 510 to detect light intensity proximate the cover glass 410 and an LCD driver 310 electrically connected to both the optical sensor 510 and the LCD shutter 210. The LCD driver 310 applies a variable shuttering voltage to the LCD shutter 210 to cause the LCD shutter 210 to increase its opacity in response to increasing light intensity detected by the optical sensor 510. This increase in opacity may be a simple change between a transparent state and a translucent state or may be a more gradual change through multiple states of increasing translucency, for more expensive systems 10. Finally, the system 10 includes battery terminals 305 adapted to electrically connect a battery to power the LCD driver 310.

The system 10 further includes a low-voltage detection module 320 and a low-voltage annunciation module 330. These modules 320, 330 might be incorporated into the LCD driver 310.

Figure 2:
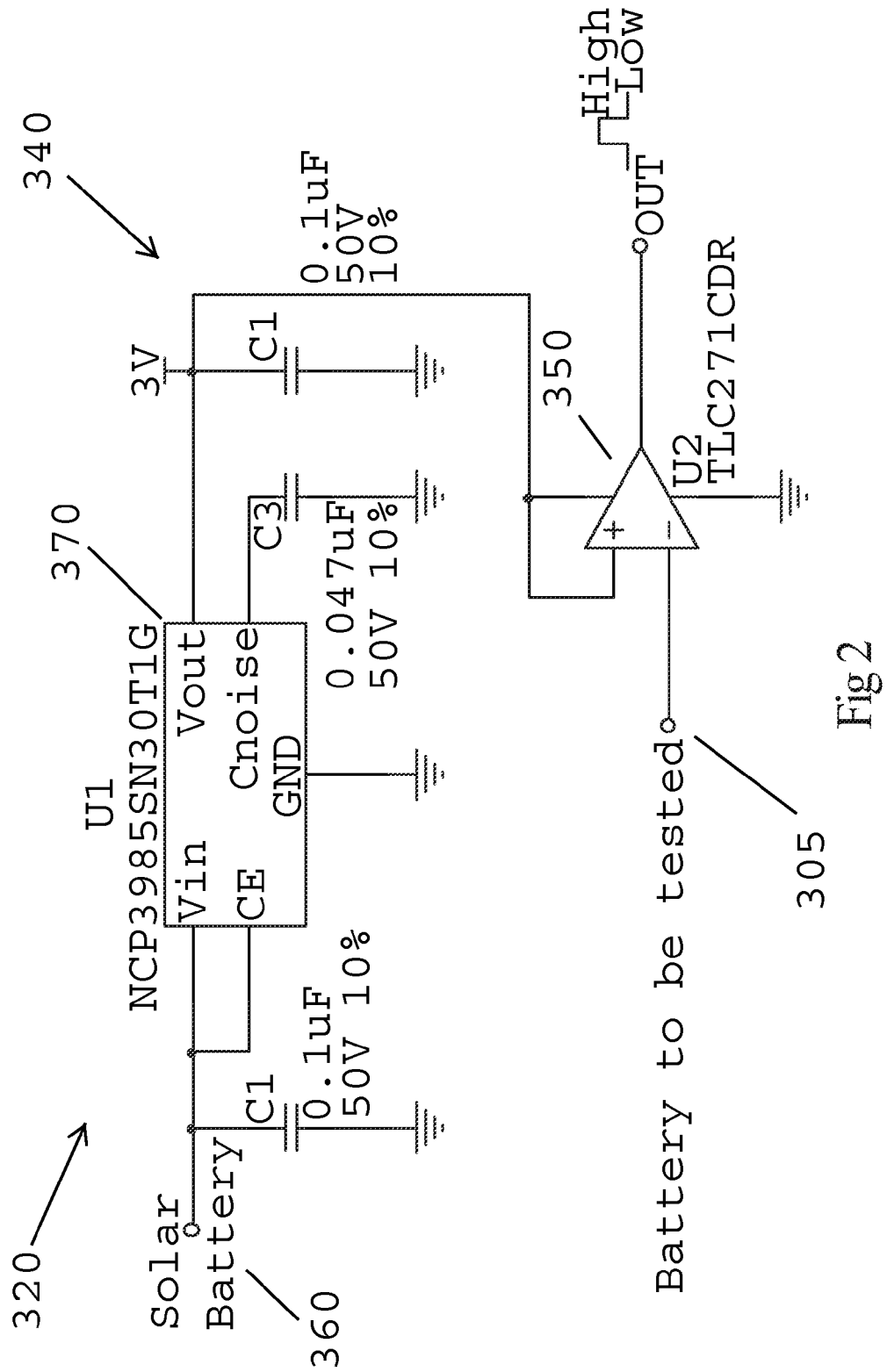
FIG. 2 is a schematic view of one embodiment of a low-voltage detection module in the LCD driver of FIG. 1.

In general terms, the low-voltage detection module 320 is configured to generate a warning signal in response to detecting low-voltage at the battery terminals 305. In that regard, the detection module 320 includes a voltage reference 340 and a comparator 350 connected between the voltage reference 340 and the battery terminals 305 to compare the voltage at the battery terminals 305 against the voltage reference 340 and to generate a corresponding signal. In the embodiment illustrated in FIG. 2, the voltage reference 340 includes a photovoltaic cell 360 and a voltage regulator 370.

In general terms, the low-voltage annunciation module 330 is configured to announce a battery low-voltage condition in response to the warning signal by applying an annunciating voltage to the LCD shutter 210 to cause the LCD shutter 210 to change its opacity.

Figure 3:
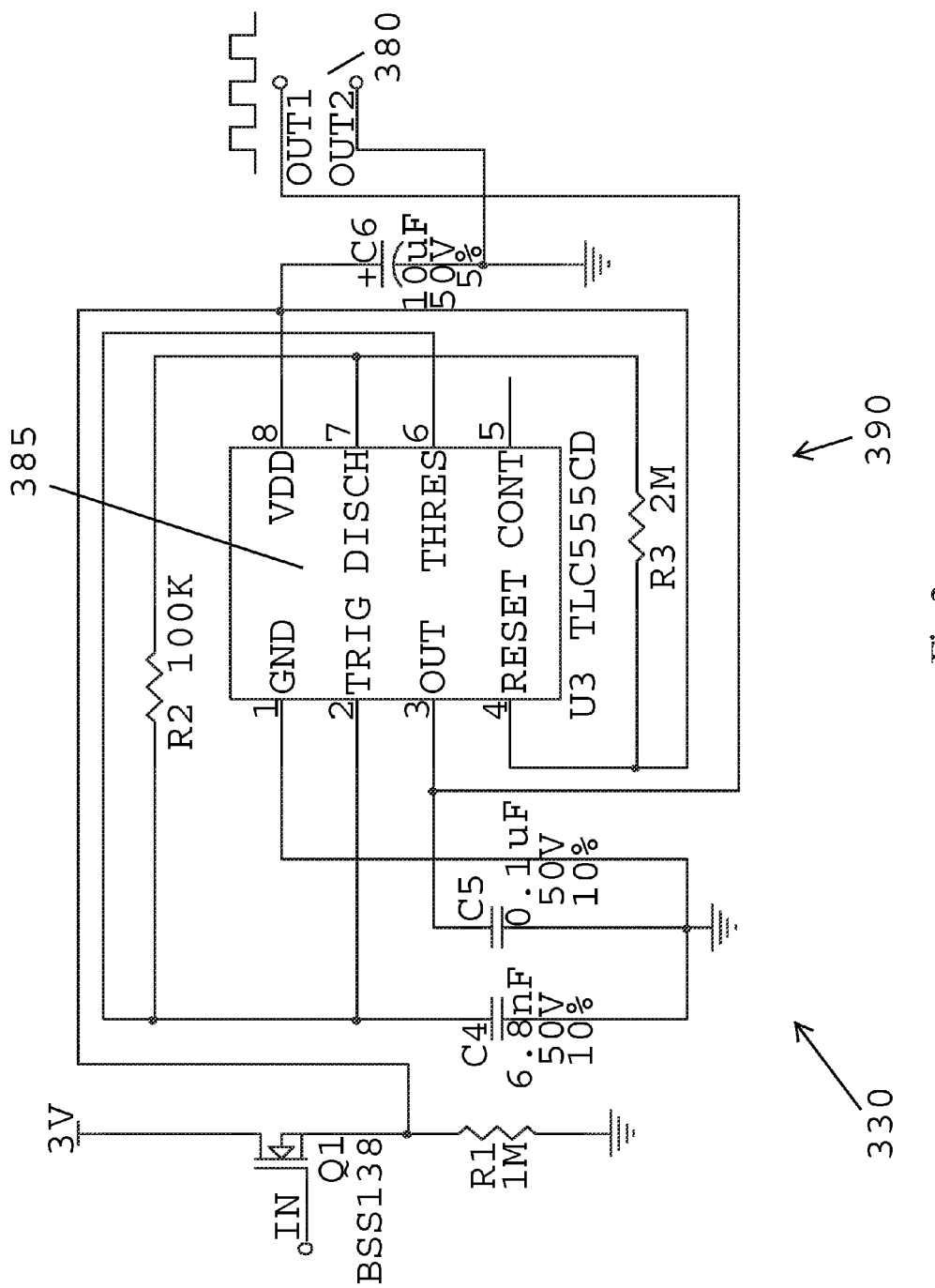
FIG. 3 is a schematic view of one embodiment of a low-voltage annunciation module in the LCD driver of FIG. 1.

In the embodiment illustrated in FIG. 3, the low-voltage annunciation module 330 includes an oscillator 380 to strobe the annunciating voltage to cause the LCD shutter 210 to periodically increase and decrease its opacity for even greater perceptibility.

In this embodiment, the oscillator 380 is embodied as the output pin of a ubiquitous TLC555CD integrated circuit 385 configured as an astable multivibrator timer circuit 390, the output pin providing the annunciation voltage to the LCD shutter 210. The reset pin of the TLC555CD integrated circuit 385 is connected to receive the warning signal from the detection module 320.

Operation.

In operation, a welder dons a welding helmet (Not Shown) having the auto-darkening optical filter module. In normal use, the optical sensor 510 monitors light intensity proximate the cover glass 410 and the LCD driver 310 applies a shuttering voltage to the LCD shutter 210 to produce an amount of opacity commensurate with the light intensity monitored. Thus, when no welding operation is ongoing, the LCD shutter 210 may be essentially transparent to permit substantially all of the ambient visible light to reach the eyes of the welder. In contrast, when a welding operation is ongoing and there is thus intense visible light proximate the cover glass 410, the LCD shutter 210 will be more opaque to reduce the portion of visible light permitted to reach the eyes of the welder.

The low-voltage detection module 320 continuously monitors the voltage of the battery at the battery terminals 305 and compares it to the voltage reference 340, which in this embodiment is set at 3V as a reasonable warning level that balances full battery consumption against a sufficient reserve during a warning to permit use of the welding helmet (Not Shown) until there is an opportunity to change the battery. In normal operation, the voltage at the battery tei ininals 305 is greater than the voltage reference 340 and the comparator 350 generates a low signal. However, as the battery is depleted through use, the voltage at the battery terminals 305 decreases and at some point it falls below the reference voltage 340, at which point the comparator 350 generates a high signal—the warning signal.

The low-voltage annunciation module 330 continuously monitors the warning signal at the reset pin of the TLC555CD integrated circuit 385. So long as the warning signal is not being generated by the detection module 320, the reset pin of the TLC555CD integrated circuit 385 is held in a low state as is the annunciating voltage at the output pin.

However, when the warning signal is being generated, the reset pin of the TLC555CD integrated circuit 385 is driven to a high state and the TLC555CD integrated circuit 385 generates a periodic annunciating voltage at its output pin.

The annunciating voltage at the output pin of the TLC555CD integrated circuit 385 is supplied to the LCD shutter 210 to change the opacity of the LCD shutter 210 as a warning that the battery voltage is low.

In this embodiment, the annunciating voltage is periodic, having a frequency between 0.1 Hz and 25 Hz. The flicker produced as the LCD shutter 210 changes opacity at that frequency is hard to ignore, and will strongly urge the welder to promptly change the battery.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. An apparatus for annunciating low-voltage in a battery supplying electricity to an auto-darkening optical filter system (10) for a welding helmet (not shown), the auto-darkening optical filter system (10) comprising:
   an optical band-pass filter (110);
   an LCD shutter (210) in series with the band-pass filter (110);
   a cover glass (410) covering the LCD shutter (210) and the band-pass filter (110);
   an optical sensor (510) for detecting light intensity proximate the cover glass (410);
   an LCD driver (310) electrically connected to the optical sensor (510) and the LCD shutter (210) and operable to apply a variable shuttering voltage to the LCD shutter (210) to cause the LCD shutter (210) to increase its opacity in response to increasing light intensity detected by the optical sensor (510); and
   battery terminals (305) adapted to electrically connect the battery to power the LCD driver (310);
   and characterized by:
   a low-voltage detection module (320) operable to generate a warning signal in response to detecting low-voltage at the battery terminals (305); and
   a low-voltage annunciation module (330), operable to announce a battery low-voltage condition in response to the warning signal by applying an annunciating voltage to the LCD shutter (210) to cause the LCD shutter (210) to change its opacity.

2. An apparatus as set forth in claim 1 wherein said low-voltage detection module (320) includes a voltage reference (340) and a comparator (350) connected between said voltage reference (340) and the battery terminals (305).

3. An apparatus as set forth in claim 2 wherein said voltage reference (340) includes a photovoltaic cell (360) and a voltage regulator (370).

4. An apparatus as set forth in claim 1 wherein said low-voltage annunciation module (330) includes an oscillator (380) to strobe the LCD shutter (210) to cause the LCD shutter (210) to periodically increase and decrease its opacity.

5. An apparatus as set forth in claim 4 wherein said oscillator (380) includes a timer circuit (390).

6. An apparatus as set forth in claim 4 wherein said oscillator (380) strobes the LCD shutter (210) at between 0.1 Hz and 25 Hz.

7. A method for annunciating low-voltage in a battery supplying electricity to an auto-darkening optical filter system (10) for a welding helmet (not shown), comprising:
   detecting low-voltage in the battery; and changing the opacity of the optical filter system (10) in response to detecting the low-voltage.

8. A method as set forth in claim 7 wherein changing the opacity means strobing the opacity.

9. A method as set forth in claim 8 wherein strobing means strobing at between 0.1 Hz and 25 Hz.

\* \* \* \* \*